US010895623B2

United States Patent
Keil et al.

(10) Patent No.: US 10,895,623 B2
(45) Date of Patent: Jan. 19, 2021

(54) METHOD FOR PERFORMING AN ANGIOGRAPHIC MEASUREMENT AND CREATING AN ANGIOGRAM

(71) Applicant: Siemens Healthcare GmbH, Erlangen (DE)

(72) Inventors: Miriam Keil, Erlangen-Dechsendorf (DE); Martin Kessner, Munich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 245 days.

(21) Appl. No.: 15/928,197

(22) Filed: Mar. 22, 2018

(65) Prior Publication Data

US 2018/0284210 A1      Oct. 4, 2018

(30) Foreign Application Priority Data

Mar. 28, 2017  (EP) .................................... 17163305

(51) Int. Cl.
*G01R 33/563* (2006.01)
*G01R 33/54* (2006.01)
(Continued)

(52) U.S. Cl.
CPC ........ *G01R 33/56316* (2013.01); *A61B 5/055* (2013.01); *G01R 33/4818* (2013.01);
(Continued)

(58) Field of Classification Search
CPC .......... G01R 33/56316; G01R 33/4818; G01R 33/543; G01R 33/546; G01R 33/5635; G01R 33/56383; A61B 5/055
(Continued)

(56) References Cited

U.S. PATENT DOCUMENTS 5,928,148 A    7/1999  Wang et al.
8,229,197 B2 * 7/2012  Schmitt .............. G01R 33/5601
                                                382/130
(Continued)

FOREIGN PATENT DOCUMENTS

DE          10230877 A1    2/2004
DE       102007009185 A1   8/2008
(Continued)

OTHER PUBLICATIONS

German Office Action dated Oct. 19, 2017 for German Application No. 17163305.0.

*Primary Examiner* — Patrick Assouad
*Assistant Examiner* — Sean Curtis
(74) *Attorney, Agent, or Firm* — Harness, Dickey & Pierce, P.L.C.

(57) ABSTRACT

A method is for performing an angiographic measurement and creating an angiogram of a body region of a patient in a magnetic-resonance system and a magnetic-resonance system for operating such a method. In an embodiment, the method includes acquisition of a body region; division of the angiographic measurement into partial angiographic measurements; displaying the measurement start times, the measurement duration and the measurement end times of the partial angiographic measurements; changing the measuring time points; definition of sequence parameters of the partial angiographic measurements based on the changed measurement start times and/or measurement end times such that the partial angiographic measurement is performable between the associated measurement start time and measurement end time; provision of the sequence parameters of the control unit of the magnetic-resonance system; performance of the partial angiographic measurements; and creation of the (Continued)

angiogram using the partial angiographic measurements performed.

23 Claims, 8 Drawing Sheets

(51) Int. Cl.
  *A61B 5/055* (2006.01)
  *G01R 33/48* (2006.01)
(52) U.S. Cl.
  CPC ......... *G01R 33/543* (2013.01); *G01R 33/546* (2013.01); *G01R 33/5635* (2013.01); *G01R 33/56383* (2013.01)
(58) Field of Classification Search
  USPC .................................. 324/300–322; 382/130
  See application file for complete search history.

(56) References Cited

U.S. PATENT DOCUMENTS

| | | | | |
|---|---|---|---|---|
| 8,975,893 | B2* | 3/2015 | Greiser | G01R 33/56316 |
| | | | | 324/309 |
| 9,462,961 | B2* | 10/2016 | Furudate | A61B 5/743 |
| 9,579,041 | B2* | 2/2017 | Miyazaki | A61B 5/201 |
| 9,675,249 | B2* | 6/2017 | Miyazaki | A61B 5/00 |
| 9,782,106 | B2* | 10/2017 | Zenge | A61B 5/055 |
| 9,974,464 | B2* | 5/2018 | Shiodera | G06F 19/321 |
| 10,258,254 | B2* | 4/2019 | Furudate | A61B 5/055 |
| 10,338,177 | B2* | 7/2019 | Kuhara | G01R 33/543 |
| 10,360,678 | B2* | 7/2019 | Jung | A61B 6/5288 |
| 2003/0095150 | A1* | 5/2003 | Trevino | G16H 40/20 |
| | | | | 715/810 |
| 2004/0008028 | A1 | 1/2004 | Horger et al. | |
| 2007/0232895 | A1 | 10/2007 | Wohlfarth | |
| 2008/0009705 | A1* | 1/2008 | Furudate | A61B 5/743 |
| | | | | 600/410 |
| 2008/0205725 | A1 | 8/2008 | Schmitt et al. | |
| 2010/0331664 | A1 | 12/2010 | Graessner | |
| 2012/0268125 | A1* | 10/2012 | Greiser | G01R 33/543 |
| | | | | 324/309 |
| 2012/0271158 | A1 | 10/2012 | Schmitt | |
| 2013/0317348 | A1* | 11/2013 | Miyazaki | A61B 5/201 |
| | | | | 600/419 |
| 2015/0097562 | A1 | 4/2015 | Grodzki et al. | |
| 2016/0054417 | A1* | 2/2016 | Kuhara | G01R 33/4818 |
| | | | | 324/309 |
| 2016/0058319 | A1* | 3/2016 | Shiodera | G06T 1/20 |
| | | | | 382/130 |
| 2016/0166172 | A1* | 6/2016 | Zenge | A61B 5/055 |
| | | | | 382/130 |
| 2016/0334486 | A9* | 11/2016 | Kuhara | G01R 33/56509 |
| 2017/0049355 | A1* | 2/2017 | Furudate | A61B 5/0037 |
| 2017/0119259 | A1* | 5/2017 | Giri | A61B 5/055 |
| 2017/0236275 | A1* | 8/2017 | Jung | A61B 6/5217 |
| | | | | 382/131 |
| 2018/0284210 | A1* | 10/2018 | Keil | G01R 33/56383 |

FOREIGN PATENT DOCUMENTS

| | | |
|---|---|---|
| DE | 102011007835 A1 | 10/2012 |
| DE | 102009031164 B4 | 11/2013 |
| DE | 102013220288 B4 | 9/2016 |
| DE | 102006006309 B4 | 1/2017 |

* cited by examiner

METHOD FOR PERFORMING AN ANGIOGRAPHIC MEASUREMENT AND CREATING AN ANGIOGRAM

PRIORITY STATEMENT

The present application hereby claims priority under 35 U.S.C. § 119 to European patent application number EP17163305.0 filed Mar. 28, 2017, the entire contents of which are hereby incorporated herein by reference.

FIELD

At least one embodiment of the invention generally relates to a method for performing an angiographic measurement and creating an angiogram of a body region of a patient in a magnetic-resonance system, wherein the body region to be examined is larger than a maximum field of view of the magnetic-resonance system and the magnetic-resonance system comprises a control unit for controlling the performance of the angiographic measurement and the creation of the angiogram, and the associated magnetic-resonance system.

BACKGROUND

In a magnetic-resonance system, typically the body to be examined of a person to be examined, in particular of a patient, is exposed to a relatively high basic magnetic field with the aid of a basic magnet, for example 1.5 or 3 or 7 tesla. Additionally, gradient pulses are played out with the aid of a gradient coil unit. Then, high-frequency radio-frequency pulses are emitted via a radio-frequency antenna unit via suitable antenna facilities, in particular excitation pulses, causing the nuclear spins of specific atoms excited to resonance by these radio-frequency pulses to be tilted by a defined flop angle relative to the magnet field lines of the basic magnetic field. Upon relaxation of the nuclear spins, radio-frequency signals, so-called magnetic-resonance signals, are emitted, received via suitable radio-frequency antennas and then processed further. Finally, the desired raw data can be reconstructed from the raw data acquired in this manner.

Contrast-enhanced magnetic-resonance tomography is a known examination method for depicting the arterial and venous vascular system. The performance of contrast-enhanced magnetic-resonance tomography is one of the more demanding tasks in medical imaging. Since magnetic-resonance systems on the market today typically have a field of view of approximately 50 cm in the longitudinal direction, during the examination, it is necessary to move the patient within the magnetic-resonance system in order, for example, to acquire the patient from the feet to the thorax.

Therefore, a measurement of this kind is divided into partial angiographic measurements, which are performed separately. The definition of the sequence parameters and the temporal sequence of the partial angiographic measurements requires special attention, in particular when a contrast medium (also called CM) is injected to enhance the signal from the blood vessels compared to the signal from the surrounding tissue and the distribution thereof in the body is to be acquired, as is the case with angiographic measurements. Data acquisition before and after contrast medium injection enables the surrounding tissue to be virtually entirely eliminated via subtraction.

Known from DE 10 2013 220 288 B4 is a method for recording magnetic-resonance image data, an image-data recording unit, a magnetic resonance device and a computer program product with which control commands for a magnetic-resonance system are optimized and checked.

DE 10 2009 031 164 B4 discloses a method for performing a multistep measurement in a magnetic-resonance system in conjunction with an angiogram.

DE 10 2011 007 835 A1 describes a method for contrast medium-free magnetic-resonance angiography requiring comparatively complex planning and DE 10 2006 006 309 B4 discloses a method with which a table is moved during the recording of data.

SUMMARY

At least one embodiment of the invention provides for a method that enables an angiographic measurement to be performed with less and more comfortable user interaction and simultaneously takes adequate account of patient variability. Advantageous embodiments are described in the claims.

The method according to at least one embodiment of the invention for performing an angiographic measurement and creating an angiogram of a body region of a patient in a magnetic-resonance system, wherein the body region is larger than a maximum field of view of the magnetic-resonance system and the magnetic-resonance system comprises a control unit for controlling the performance of the angiographic measurement and the creation of the angiogram, comprises: acquisition of an anatomical size of the patient and an upper limit and a lower limit of the body region, division of the angiographic measurement into partial angiographic measurements, wherein the control unit divides the body region into a plurality of partial measuring ranges to be measured in succession, wherein each partial measuring range is assigned to different body regions, wherein each partial measuring range is no larger than the maximum field of view and in each case is assigned to a partial angiographic measurement and wherein each partial angiographic measurement is assigned measuring time points, including in each case a measurement start time and a measurement end time, so that an overall measurement duration of the angiographic measurement is defined by the measurement start time of the first partial angiographic measurement and the measurement end time of the last partial angiographic measurement, displaying the measurement start times, the measurement duration and the measurement end times of the partial angiographic measurements on a graphical user interface, changing the measuring time points, wherein a change in a measuring time point of a partial angiographic measurement automatically causes an adaptation of at least one further measuring time point of another partial angiographic measurement, definition of sequence parameters of the partial angiographic measurements based on the changed measurement start times and/or measurement end times such that the partial angiographic measurement can be performed between the associated measurement start time and measurement end time, provision of the sequence parameters of the control unit of the magnetic-resonance system, performance of the partial angiographic measurements, and creation of the angiogram using the partial angiographic measurements performed.

In addition to the method, at least one embodiment of the invention also relates to a magnetic-resonance system embodied to perform the method according to at least one embodiment of the invention embodied and in which a contrast medium injection apparatus is integrated. The above statements relating to the method according to embodiments of the invention can be transferred analogously to the magnetic-resonance system.

Hence, in at least one embodiment, the magnetic-resonance system is designed to carry out a method for performing an angiographic measurement and creating an angiogram of a body region of a patient, wherein the body region is larger than a maximum field of view of the magnetic-resonance system and the magnetic-resonance system comprises a control unit for controlling the performance of the angiographic measurement and the creation of the angiogram.

The magnetic-resonance system can further comprise control components, which are necessary and/or advantageous for carrying out a method according to at least one embodiment of the invention. A storage unit of the planning unit and/or the control unit and/or the measuring unit can also store computer programs and further software by which a processor of the planning unit and/or the control unit and/or the measuring unit automatically controls or carries out a procedural sequence of a method according to at least one embodiment of the invention.

BRIEF DESCRIPTION OF THE DRAWINGS

Further advantages and details of the present invention can be derived from the example embodiments described in the following and with reference to the drawings, in which.

DETAILED DESCRIPTION OF THE EXAMPLE EMBODIMENTS

Figure 1:
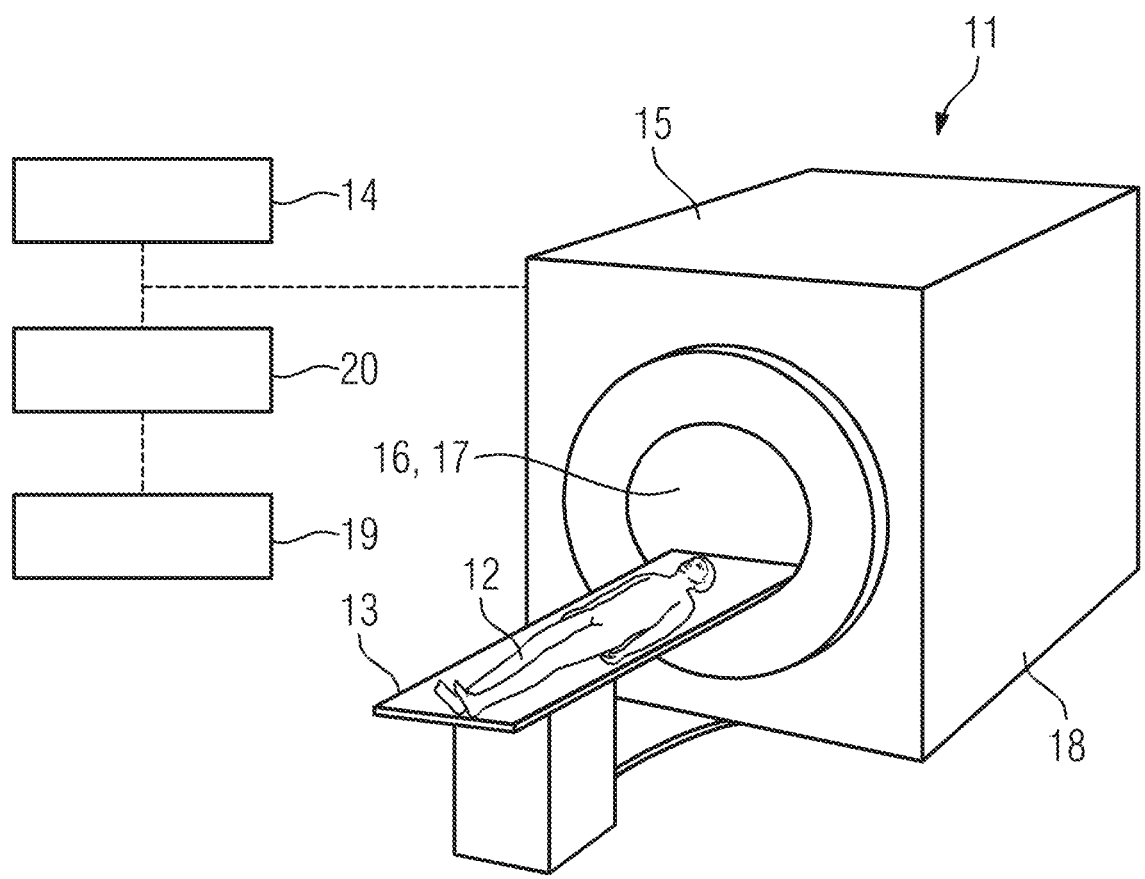
FIG. 1 shows a magnetic-resonance system according to an embodiment of the invention in a schematic representation.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for performing an angiographic measurement and creating an angiogram of a body region of a patient in a magnetic-resonance system, wherein the body region is larger than a maximum field of view of the magnetic-resonance system and the magnetic-resonance system comprises a control unit for controlling the performance of the angiographic measurement and the creation of the angiogram, comprises:

acquisition of an anatomical size of the patient and an upper limit and a lower limit of the body region, division of the angiographic measurement into partial angiographic measurements, wherein the control unit divides the body region into a plurality of partial measuring ranges to be measured in succession, wherein each partial measuring range is assigned to different body regions, wherein each partial measuring range is no larger than the maximum field of view and in each case is assigned to a partial angiographic measurement and wherein each partial angiographic measurement is assigned measuring time points, including in each case a measurement start time and a measurement end time, so that an overall measurement duration of the angiographic measurement is defined by the measurement start time of the first partial angiographic measurement and the measurement end time of the last partial angiographic measurement, displaying the measurement start times, the measurement duration and the measurement end times of the partial angiographic measurements on a graphical user interface, changing the measuring time points, wherein a change in a measuring time point of a partial angiographic measurement automatically causes an adaptation of at least one further measuring time point of another partial angiographic measurement, definition of sequence parameters of the partial angiographic measurements based on the changed measurement start times and/or measurement end times such that the partial angiographic measurement can be performed between the associated measurement start time and measurement end time, provision of the sequence parameters of the control unit of the magnetic-resonance system, performance of the partial angiographic measurements, and creation of the angiogram using the partial angiographic measurements performed.

Typically, in addition to the division of the body region to be examined into geometric partial measuring ranges, particular importance is attached to the definition of the temporal sequence of the angiographic measurement in order to synchronize the time of the data acquisition exactly with the contrast medium injection, so that the contrast medium bolus passes through the partial measuring range during the data acquisition. Therefore, it is in particular necessary for the sequence parameters and in particular in the measuring time points, such as measurement duration, measurement start times and measurement end times of the assigned partial angiographic measurements to be adapted in order to take adequate account of patient-specific characteristics, such as the contrast medium circulation time and the size of the patient.

To ensure that the arteries are not superimposed by the veins, it is also necessary for the angiographic measurement to be performed before the perfusion of the contrast medium in the veins (reflux). To date, typically the angiographic measurement has been performed via complex and extensive interaction with the user, who has had to define both the geometry via the partial measuring ranges of the angiographic measurement and the temporal sequence of assigned partial angiographic measurements of the angiographic measurement in each case such that the partial measuring ranges of the partial angiographic measurements lie in the maximum field of view of the magnetic-resonance system.

To support the procedure, typically contrast medium dynamics are acquired in the abdomen and on the basis thereof, for example, the partial measuring range 'abdomen' adapted with the corresponding partial angiographic measurement. Either for reasons of time or due to a lack of technical knowledge on the part of the user, typically there would be no adaptation of the other partial measuring ranges to the patient's physiology (for example, to contrast medium dynamics, in particular to the circulation time of the contrast medium). In particular, this adaptation of the measuring time points to the contrast medium dynamics is a task that can require a plurality of user-interaction-steps, which are performed in a plurality of substeps, in particular in dependence on the number of partial angiographic measurements. Automatic adaptation of a measuring time point as soon as another measuring time point is changed enables the angiographic measurement to be performed more quickly and comfortably because fewer user-interaction steps are required for the adaptation of the measuring time points to, for example, the partial measuring ranges, the patient's circulation time and in particular the contrast medium dynamics.

In addition, the sequence parameters of the partial angiographic measurements are defined automatically which also enables the angiographic measurement to be performed more simply. In particular, the decision as to which of the plurality of adjustment and configuration possibilities is to be selected could overtax users and occupy them for a longer time. This time requirement occurred with each individual adaptation of the geometry of the partial measuring ranges or the temporal sequence of the partial angiographic measurements. Now, sequence parameters of the partial angiographic measurements are defined automatically, in particular on each change of the measuring time point and on the associated automatic adaptation of the further measuring time point. This enables optimal and simple performance of the angiographic measurement, in particular when the user does not have extensive knowledge of sequence parameters and other settings during an angiographic measurement.

An anatomical size of the patient can in particular be acquired by the user on the graphical user interface or alternatively automatically by way of determination using landmarks. The height of the patient from the sole of the foot to the top of the head is an expedient anatomical size of the patient. Typically, the height and weight are determined in the case of measurements in magnetic-resonance systems in order to be able to determine the patient's specific absorption rate. The height and the weight of the patient can for example be input manually by a user, for example directly during the angiographic measurement to be performed or, in a further embodiment, transferred automatically from a patient record to which the magnetic-resonance system has access.

An examination region typically represents a volume, in particular the body region, which is to be depicted via the magnetic-resonance system. The examination region is typically defined by a user, for example on an overview (localizer) by the acquisition of an upper limit and a lower limit of the body region. In one embodiment, the examination region can alternatively be defined via a selection of body regions shown in a list on the graphical user interface. The patient's body can expediently be divided according to the patient's anatomy into different body regions such as thigh, lower leg, abdomen etc. In a further embodiment, the examination region is defined on the graphical user interface in a schematic diagram corresponding to a human body and typically divided according to the position of body regions. For example, the examination region can also be transferred automatically from the appointment schedule. Expediently, when the body regions are selected in the list or for example in the schematic diagram on the graphical user interface, the examination region is automatically assigned either standard positions or patient positions as the upper limit and the lower limit of the body region according to the selected body regions using landmarks acquired on overviews, for example on the localizer for the patient.

The maximum field of view of the magnetic-resonance system, also called the FOV, in particular also the maximum extension of the FOV in the z-direction of the magnetic-resonance system includes a volume within which measurements can be performed in a magnetic-resonance system, in particular partial angiographic measurements, without table feed or repositioning of the patient. Since the body region of angiographic measurement is typically larger than the maximum field of view of the magnetic-resonance system, the control unit divides the body region into a plurality of partial measuring ranges and in each case arranges the partial measuring ranges in the maximum field of view of the magnetic-resonance system. The partial measuring ranges of the body region in particular together form the entire examination region, which is larger than the maximum field of view of the magnetic-resonance system.

Preferably, the control unit arranges the partial measuring ranges such that the partial measuring ranges expediently partially overlap at the edges of the partial measuring ranges. The control unit divides the body region into a plurality of partial measuring ranges preferably automatically, wherein the division can, for example, also be performed by the user on the graphical user interface. It is also possible for a partial measuring range be modified, for example with respect to the volume in question.

In addition, the angiographic measurement is, preferably automatically, divided into partial angiographic measurements if the region defined by the upper limit and the lower limit of the body region is larger than the maximum field of view of the magnetic-resonance system. Typically, each partial measuring range, which was defined in accordance with the division of the body region according to the preceding embodiment is assigned a partial angiographic measurement.

Each partial angiographic measurement is assigned measuring time points, at least one measurement start time as the measurement start of the partial angiographic measurement and a measurement end time as the measurement end of the partial angiographic measurement, wherein the difference between the measurement end time and measurement start time of the measurement duration corresponds to the partial angiographic measurement. Each partial angiographic measurement assigned to a different partial measuring range typically differs from the other partial angiographic measurements in the measuring time points, in particular in the measurement start time and in the measurement end time, because the partial angiographic measurements can often only be performed in sequence. The partial angiographic measurement with the earliest measurement start time preferably corresponds to the first partial angiographic measurement and the partial angiographic measurement with the latest measurement start time to the last partial angiographic measurement.

The overall measurement duration of the angiographic measurement is defined by the measurement start time of the first partial angiographic measurement and the measurement end time of the last partial angiographic measurement. Typically, pauses in measurement times are arranged between the partial angiographic measurements. The overall measurement duration is obtained from the sum of the measurement duration of the partial angiographic measurements and the pauses in measurement times.

A measurement time pause is characterized by the interval between the measurement end time of the preceding partial angiographic measurement and the measurement start time of the subsequent partial angiographic measurement and is preferably kept as short as possible. The length of the measurement time pause is in particular dependent upon the technical design of the magnetic-resonance system, for example the maximum field of view and the table feed rate. The length of the measurement time pause can also be dependent on the time required to play out audible breathing commands to hold the breath or to resume breathing or for adjustment measures for subsequent partial angiographic measurements.

For example, the partial angiographic measurement in the assigned partial measuring range 'abdomen' can require breathing commands to hold the breath or to resume breathing, while the partial angiographic measurement in the assigned partial measuring range 'feet' does not require any breathing commands. In this case, the measurement time pause before the partial angiographic measurement in the partial measuring range 'feet' can be shorter than if the breathing command to hold the breath were necessary. During the measurement time pause, the patient is, for example, diverted by a table feed such that the partial measuring range assigned to the subsequent partial angiographic measurement is positioned in the field of view of the system. Alternatively, the patient can be relocated. For each overall measurement duration with a number N of partial angiographic measurements, there are typically (N−1) pauses in measurement times, one between each two partial angiographic measurements.

Each partial angiographic measurement typically includes exactly one measurement in the assigned partial measuring range in a magnetic-resonance system. The partial angiographic measurements are preferably arranged in a time sequence such that the sequence of the partial angiographic measurements follows the expected course of the contrast medium in the patient. Expediently, the measurement duration of the partial angiographic measurements is also matched to the patient's contrast medium dynamics. In particular, suitable algorithms can be used to ascertain the angiogram of the patient after the performance of the partial angiographic measurements. Particularly advantageous is automatic division into partial angiographic measurements, wherein the performance of the partial angiographic measurements is simplified.

Typically, the measurement start times, the measurement duration, the measurement end times of the partial angiographic measurements, the overall measurement duration and a bolus delay are displayed on a graphical user interface preferably on a timeline. The display can, for example, include a monitor. The timeline is preferably embodied as a horizontal axis. The bolus delay typically corresponds to the difference between the bolus injection and the measurement start time of the first partial angiographic measurement, wherein not every partial angiographic measurement requires a bolus injection. For example, fewer or also additional relevant parameters are displayed for the performance of the angiographic measurement. In addition, it is possible for a measurement box to be displayed for each partial angiographic measurement over the timeline the width of which is defined by the measurement start time and the measurement end time of the partial angiographic measurement.

Typically, it is possible for the measuring time points of the partial angiographic measurements to be changed. The measuring time points can preferably be changed by user interaction steps with the graphical user interface. The change can mean displacement along of the timeline by selecting a measuring point with an input device and the subsequent release of the measuring point, typically also called "drag-and-drop". Alternatively, the user can also determine a shift of a measuring time point along the timeline by inputting a numerical value or selecting automatically prespecified values. Other forms of user interaction on or with the graphical user interface are conceivable. In particular, changing the measuring time points means that the time point assigned to a measuring time point, which, for example, corresponds to the measurement start and the measurement end of the partial angiographic measurement, changes. The advantage of changing the measuring time points on the graphical user interface is ease of handling and adaptation of the partial angiographic measurements by the user.

Typically, each partial angiographic measurement comprises sequence parameters. The sequence parameters can preferably be defined automatically but can also be defined by the user on the graphical user interface. For example, the anatomical size of the patient influences the size and alignment of the partial measuring ranges and the assigned body region influences the preferably automatic definition of the sequence parameters. Expediently, several sequence parameters are adapted for the performance of the angiographic measurement in respect of contrast, signal strength and measurement duration. The sequence parameters can typically be adapted more than once, preferably also after each change of measuring time points such that the partial angiographic measurements can be performed within the respective measuring time points. This adaptation can preferably be performed automatically in the background, i.e. so it is not directly visible to the user.

Expediently, the sequence parameters of the respective partial angiographic measurement are defined such that partial angiographic images required to create the angiogram can be ascertained based on the partial angiographic measurements. For example, extending the measurement duration of a partial angiographic measurement can enhance the image quality, for example at the expense of the image quality of another partial angiographic measurement of which the measurement duration is reduced. Inter alia, a resolution and a slice thickness of the partial angiographic measurement can be relevant for the image quality.

In addition to the above-described direct change to the measuring time points of the partial angiographic measurements by the user, it is also possible for the measuring time points of the partial angiographic measurements to be changed indirectly in that, for example, the user changes or defines certain sequence parameters of the partial angiographic measurements. This is used as the basis for adapting one or more measuring time points of the partial angiographic measurements. For example, if the user defines a lower number of slices to be measured in a partial angiographic measurement, the measurement duration of the one partial angiographic measurement is reduced and the measurement duration of the subsequent and/or preceding partial angiographic measurement is extended to the same degree. Preferably, the extension of the measurement duration of the subsequent and/or preceding partial angiographic measurement causes the sequence parameters to be automatically defined.

Automatic definition of the sequence parameters is particularly advantageous, wherein for each patient, high image quality is ensured with optimal adaption between the bolus injection and the partial angiographic measurements. This can avoid the need to repeat partial angiographic measurements as the result of non-optimal definition of the sequence parameters and the temporal sequence of the angiographic measurement. Repetition can be time-consuming and can also present a risk to the patient due to the repeat administration of contrast medium. Automatic definition of the sequence parameters also enables users who do not have extensive knowledge of sequence parameters or other settings to ascertain reliably good angiograms of the patient. Alternatively, specific sequence parameters can also be defined while observing specific user specifications or by derivation from the patient record. For example, the user can define specific sequence parameters freely and independently of specifications.

Herein, it is possible for specific sequence parameters of a partial angiographic measurement to be kept invariable. This can, for example, be sequence parameters that influence the contrast of the partial angiographic images ascertained on the basis of the partial angiographic measurements. Other sequence parameters of the partial angiographic measurement can be set as variable. This can, for example, be sequence parameters that influence the slice distance and the resolution. The sequence parameters that are kept variable are ascertained automatically subject to the boundary condition that the partial angiographic measurement must be completed within the specified measurement duration. This can in particular take place subject to the proviso of maintaining the highest possible high image quality.

The sequence parameters of the partial angiographic measurement of the control unit of the magnetic-resonance system are in particular provided to perform the partial angiographic measurements. The sequence parameters of the control unit are preferably provided automatically.

Expediently, the partial angiographic measurements are performed automatically, wherein the associated partial measuring ranges are in each case positioned in the maximum field of view of the system. For example, each partial angiographic measurement can also be performed several times, preferably without adaptation of the sequence parameters. During the angiographic measurement, typically a first performance of the partial angiographic measurements is followed by a second performance of the partial angiographic measurements.

In particular, the contrast medium bolus is injected after the first performance of the (pre-CM)partial angiographic measurements and before the second performance of the (post-CM)partial angiographic measurements. For example, the injection can be given via an injector. The time point of the injection can typically be defined by the user or automatically in the sequence of the partial angiographic measurements. For example, the partial measuring ranges are therefore measured twice in each case with the pre-CM partial angiographic measurements and the post-CM partial angiographic measurements, wherein preferably there is no difference between the sequence parameters of the pre-CM partial angiographic measurements and the post-CM partial angiographic measurements. As a result, the overall measurement duration of the pre-CM partial angiographic measurements is preferably identical to the overall measurement duration of the post-CM partial angiographic measurements.

Typically, the angiogram is created using the partial angiographic measurements performed. Preferably, partial angiographic images are ascertained based on the partial angiographic measurements in order to create the angiogram of the patient by way of the partial angiographic images. For this, it can be advantageous for there to be spatial overlapping of the partial measuring ranges. Typically, the angiogram of the patient is created from the difference between the pre-CM partial angiographic images and the post-CM partial angiographic images. In this case, the angiogram substantially only corresponds to contrast medium dynamics within the patients' blood vessels. The angiogram is preferably created automatically based on the partial angiographic images of the partial angiographic measurement in the partial measuring regions via suitable algorithms. Alternatively, the user can also observe the partial angiographic images separately on the graphical user interface or combine them manually to form the angiogram of the patient.

In one embodiment, changing the measurement end time of the non-last partial angiographic measurement can cause the measurement start time of the subsequent partial angiographic measurement to be changed automatically. For example, changing the measurement end time of the first partial angiographic measurement causes the measurement start time of the second partial angiographic measurement to be changed. Changing the measurement end time of the non-last partial angiographic measurement can also only cause the measurement start time of the subsequent partial angiographic measurement to be changed automatically. Changing the measurement end time of the non-last partial angiographic measurement can also take place such that the measurement start time of the subsequent partial angiographic measurement is changed in accordance with the difference between the changed measurement end time before and after the change. This in particular means that the overall measurement duration and the sum of the measurement duration of the partial angiographic measurements remain constant.

In a further embodiment, changing the measurement start time of the non-first partial angiographic measurement can cause the measurement end time of the preceding partial angiographic measurement to be changed automatically. For example, changing the measurement start time of the second partial angiographic measurement causes the measurement end time of the first partial angiographic measurement to be changed. Alternatively, changing the measurement start time of the non-first partial angiographic measurement can only cause the measurement end time of the preceding partial angiographic measurement to be changed automatically. Changing the measurement start time of the non-first partial angiographic measurement can also that place such that the measurement end time of the preceding partial angiographic measurement is changed in accordance with the difference between the changed measurement start time before and after the change. This in particular means that the overall measurement duration and the sum of the measurement duration of the partial angiographic measurements remain constant.

In a further embodiment, the measurement end times of all partial angiographic measurements and the measurement start times of all except for the first partial angiographic measurement are changed by changing the measurement end time of the last partial angiographic measurement. This in particular means that the overall measurement duration is changed in accordance with the change in the measurement end time of the last partial angiographic measurement. Preferably, changing the measurement end time of the last partial angiographic measurement in particular causes the measurement duration of all partial angiographic measurements to change and the pauses in measurement times, i.e. the interval between the measurement end time of the preceding partial angiographic measurement and the measurement start time of the subsequent partial angiographic measurement, remain unchanged.

For example, changing the measurement end time of the last partial angiographic measurement can cause the measurement duration of all partial angiographic measurements to change relative to their proportional share in the overall measurement duration or proportionally in accordance with a weighting according to the measurement duration of the partial angiographic measurements. In addition, the measurement duration of the partial angiographic measurement can also take place based on weightings, which are based not on the measurement duration of the partial angiographic measurements but on user-defined or automatically specified factors.

In a further embodiment, changing the measurement start time of the first partial angiographic measurement, causes the measurement start times and the measurement end times of all partial angiographic measurements to be automatically changed, in particular without changing the overall measurement duration and the measurement durations relative to one another. Preferably, the measurement start times and the measurement end times of all partial angiographic measurements —hence also the pauses in measurement times—are automatically changed to the degree of the change in the measurement start time of the first partial angiographic measurement. For example, this results in measuring time points of the partial angiographic measurement shifting by the same time. Changing the measurement start time of the first partial angiographic measurement in particular causes pauses in measurement times between the partial angiographic measurements to be kept constant.

In one embodiment, simultaneously changing the measurement start time and the measurement end time of a partial angiographic measurement or the measurement end time of a preceding partial angiographic measurement and the measurement start time of a subsequent partial angiographic measurement causes a change in the measurement start time and the measurement end time of all partial angiographic measurements. Simultaneously changing the measurement end time of a preceding partial angiographic measurement and the measurement start time of a subsequent partial angiographic measurement in particular corresponds to a shift of the measurement time pause.

Two measuring time points can, for example, be changed simultaneously by "drag-and-drop", preferably such that a region lying between a preceding measurement end time and a subsequent measurement start time or between a preceding measurement start time and a subsequent measurement end time is shifted. For example, shifting a measurement box of a partial angiographic measurement, corresponding to the simultaneous shifting of a preceding measurement start time and a subsequent measurement end time, along the timeline can automatically shift the measurement start time and the measurement end time of the associated partial angiographic measurement and all measuring time points of the other partial angiographic measurements simultaneously to the same degree so that the overall measurement duration and the proportional share of the pauses in measurement times in the overall measurement duration remains constant.

One embodiment provides that the body region includes at least the body regions 'abdomen', 'thigh' and 'lower leg'. In particular, the body region can also include the body region 'kidneys', wherein typically the body region 'abdomen' also covers the kidneys. Preferably, the body region is divided into at least a first partial measuring range 'abdomen', a second measuring range 'thigh' and a third partial measuring range 'lower leg' with in each case a first partial angiographic measurement 'abdomen', a second partial angiographic measurement 'thigh' and a third partial angiographic measurement 'lower leg'. Typically, the partial measuring ranges acquire at least a part of the assigned body regions, however also parts of body regions to which the respective partial measuring range is not assigned. For example, the first partial measuring range 'abdomen' can also include the thorax or the third partial measuring range can also include the feet. Alternatively, the body region can also be divided into a plurality of, for example, four, partial measuring ranges with an additional fourth partial measuring range 'feet' with a fourth assigned partial angiographic measurement 'feet'. The number of partial measuring ranges, and hence also the number of partial angiographic measurements, is variable and can be defined and displayed individually for each patient.

In a further embodiment, the measuring time points of the partial angiographic measurements preferably each include a mid-time point, wherein said time point corresponds to an acquisition of a center of a k-space. The mid-time point corresponds to the time point at which the partial angiographic measurements preferably each acquire a center of the k-space. In particular, the center of the k-space can contain the low-frequency components of the partial angiographic measurement, compared to the high-frequency components of the partial angiographic measurement, in the peripheral part of the k-space. The center of the k-space is therefore preferably responsible for the contrast, while the periphery of the k-space tends to be responsible for the details of the partial angiographic measurement.

For example, a mid-time point of a partial angiographic measurement is displayed on the graphical user interface. The mid-time point can be changed between the measurement start time and the measurement end time of the partial angiographic measurements. This corresponds to a change on the graphical user interface within the limits of the associated measurement box. Expediently, it is possible for such regions within the measurement box that cannot be implemented with a pulse sequence or with the sequence parameters calculated in the background to be automatically excluded. In a further embodiment, alternatively, it could only be possible to change the mid-time point in such a region subject to specific provisos, for example, it would then be necessary to change the other measuring time points. Alternatively, at least one mid-time point can be displayed but not changed by the user.

In a further embodiment, it is additionally possible for the contrast medium dynamics of the patient to be displayed on the graphical user interface. The contrast medium dynamics are preferably acquired on at least one station of a vascular structure via a test bolus measurement, preferably before the division of the angiographic measurement into partial angiographic measurements. The vascular structure at least partially includes the patient's blood vessels. The test bolus measurement is a series of short individual measurements that enable the temporal course of the contrast medium to be acquired. During the performance of the test bolus measurement, with which preferably a test bolus is injected, test bolus-contrast-medium dynamics images are acquired, for example also via algorithms, which can highlight the contrast medium dynamics or the like. The test bolus can have a lower quantity of contrast medium compared to the contrast medium bolus injected during the subsequent partial angiographic measurements. A contrast-medium course, in particular the contrast medium dynamics, can be derived from the test bolus-contrast-medium-dynamics contrast-medium-dynamics images.

The definition of at least one station is typically performed either automatically or by the user using the evaluation of the test bolus-contrast-medium-dynamics images. For example, when defining the at least one station, the user takes the anatomy of the patient into account. The contrast medium dynamics can preferably be acquired at two stations, wherein in each case a first station is close to the first limit and a second station is close to the second limit of the body region. The first station will generally include patient's abdomen. Expediently, the second station includes either the lower leg or preferably the feet, because the transition between arterial blood vessels and venous blood vessels is typically shorter there than in the abdomen. The contrast medium dynamics can be acquired on two arterial stations, which were defined, for example, automatically or by the user.

Since, the vascular structure typically includes both arterial blood vessels, in particular arteries, and venous blood vessels, in particular veins, the contrast medium dynamics can be acquired on at least one arterial station and one venous station. An arterial station preferably includes at least one arterial blood vessel and a venous station at least one venous blood vessel. For example, the first station can correspond to the arterial station and the second station to the venous station. The test bolus measurement can preferably be used to measure the arterial phase of the injected test bolus at the first station and the venous phase of the injected test bolus at the second station. However, it is in principle also possible for both the arterial phase and the venous phase or only the arterial phase or only the venous phase to be measured at each station during the test bolus measurement if, in particular, a measurement duration and a measurement start time of the test bolus measurement and the time point of the injection of the test bolus are defined accordingly.

A partial measuring range can typically include a station. Preferably, therefore, the measurement end times of the partial angiographic measurements can be defined such that the partial angiographic measurements can be performed before the onset of the venous phase of the injected bolus at the stations of the partial measuring ranges assigned to the respective partial angiographic measurements. The contrast medium dynamics can in particular be acquired at the arterial station in the arterial phase of the test bolus and at the venous station in the arterial phase of the test bolus. This is in particular advantageous because this enables a venous overlapping of arterial vessels to be avoided. Venous overlapping of the arterial vessels can complicate, and sometimes completely prevent, diagnosis using the angiographic measurement because, for example, diagnosis in particular requires the acquisition of the arterial vessels during the angiographic measurement.

In one embodiment, the contrast medium dynamics acquired via the test bolus measurement are taken into account on the division of the angiographic measurement into partial angiographic measurements because the contrast medium dynamics typically differ from patient to patient. It is also possible for the contrast medium dynamics to vary in the same patient depending upon which respective partial measuring range includes the station at which the contrast medium dynamics were acquired. On the division of the angiographic measurement into partial angiographic measurements, one partial angiographic measurement with a first contrast medium velocity derived from contrast medium dynamics is assigned a shorter measurement duration than a partial angiographic measurement with a second, slower, contrast medium velocity derived from the contrast medium dynamics.

For example, the first contrast medium velocity of the patient is higher than the second contrast medium velocity of another patient in another other angiographic measurement. In this case, the partial angiographic measurement of the patient can be assigned a shorter measurement duration than the partial angiographic measurement of the further patient in the other angiographic measurement. In a further example, the first contrast medium velocity of the patient differs from the second contrast medium velocity of the patient, wherein the first contrast medium velocity and the second contrast medium velocity were acquired at stations in the respective different partial measuring regions assigned. Therefore, the measurement duration of the partial angiographic measurements can be defined in dependence on the respective contrast medium velocity, which was acquired in the different partial measuring regions assigned.

Alternatively or additionally, it is also possible to take account of other parameters derived from the contrast medium dynamics such as, for example, a maximum-value time point of the course of the contrast medium corresponding to the time point of the maximum contrast medium accumulation or a circulation time of the contrast medium for the transport of the contrast medium. The contrast medium velocity can typically be converted into the circulation time of the contrast medium and the circulation time of the contrast medium into the contrast medium velocity.

According to a further embodiment, it is, for example, possible for the contrast medium dynamics, the measuring time points, in particular the measurement start times, the measurement duration, the measurement end times and the mid-time points of the partial angiographic measurements, to be displayed superimposed on the graphical user interface, preferably such that the measuring time points correspond to a part of the measurement box and the measurement time pause corresponds to the interspace between the measurement boxes. Additionally, the contrast medium dynamics can preferably be displayed such that the course of the contrast medium can be displayed for each station. For example, it is possible, therefore, to display the course of the contrast medium at the arterial station and the venous station. Alternatively or additionally, it is also possible for the course of the contrast medium during the arterial phase of the test bolus and the course of the contrast medium during the venous phase of the test bolus to be displayed. It is typically advantageous to match the mid-time points of the partial angiographic measurements to at least one maximum-value time point. This can ensure a high signal and strong contrast during the performance of the partial angiographic measurements.

In one embodiment, it is additionally possible for symbols to be displayed on the graphical user interface along the time axis, for example as an indicator to hold the breath and to resume breathing. The time points of these symbols can be changed by the user, in particular when the user defines the measuring time points of the partial angiographic measurements. Typically, the time points for holding the breath and resumption of breathing depend upon the partial angiographic measurements. Then, during the actual performance of the partial angiographic measurements, corresponding breathing commands are played out at the time points.

It is also additionally possible for a symbol to mark the time point of the contrast medium injection. The time point of the contrast medium injection is typically defined as $t=0$ s. The measuring time points are then played out during the performance of the partial angiographic measurements based on the time point of the contrast medium injection. In particular, it is also possible for the maximum-value time point and a difference between the maximum-value time point and the mid-time point of the partial angiographic measurements to be displayed. The difference between the maximum-value time point and the mid-time point in particular corresponds to the time interval. The input of a numerical value by the user on the graphical user interface can cause the difference between at least one maximum-value time point of the contrast medium dynamics and the mid-time point of the partial angiographic measurements to be adapted. It is in particular advantageous for the mid-time point of the partial angiographic measurements to be changed such that the interval between the maximum-value time point and the mid-time point of the partial angiographic measurements is reduced or in particular such that the mid-time point of the partial angiographic measurement is closer to the measurement start time than to the measurement end time of the respective partial angiographic measurement.

In a further embodiment, the display to be shown on the graphical user interface can be specified by the user or also automatically. Alternatively, the user can, for example, partially fade-in and fade-out specific measuring times.

In addition to the method, at least one embodiment of the invention also relates to a magnetic-resonance system embodied to perform the method according to at least one embodiment of the invention embodied and in which a contrast medium injection apparatus is integrated. The above statements relating to the method according to embodiments of the invention can be transferred analogously to the magnetic-resonance system.

Hence, in at least one embodiment, the magnetic-resonance system is designed to carry out a method for performing an angiographic measurement and creating an angiogram of a body region of a patient, wherein the body region is larger than a maximum field of view of the magnetic-resonance system and the magnetic-resonance system comprises a control unit for controlling the performance of the angiographic measurement and the creation of the angiogram.

The magnetic-resonance system can further comprise control components, which are necessary and/or advantageous for carrying out a method according to at least one embodiment of the invention. A storage unit of the planning unit and/or the control unit and/or the measuring unit can also store computer programs and further software by which a processor of the planning unit and/or the control unit and/or the measuring unit automatically controls or carries out a procedural sequence of a method according to at least one embodiment of the invention.

The magnetic-resonance system with the planning unit, the control unit and the measuring unit is designed such that the performance of the angiographic measurement of a body region takes place via partial angiographic measurements, wherein the plurality of partial measuring ranges, which are in each case assigned one of the partial angiographic measurements, are parts of this one body region.

The magnetic-resonance system with the planning unit, the control unit and the measuring unit is designed such that the performance of the angiographic measurement of a body region takes place via partial angiographic measurements, wherein the measuring time points of the partial angiographic measurements are changed such that, on the change of a measuring time point, at least one further measuring time point is changed automatically.

The magnetic-resonance system with the planning unit, the control unit and the measuring unit is designed such that the performance of the angiographic measurement of a body region is performed via partial angiographic measurements, wherein the measuring time points of the partial angiographic measurements are defined automatically, preferably based on an anatomical size and/or contrast medium dynamics of the patient.

FIG. 1 is a schematic representation of a magnetic-resonance system according to an embodiment of the invention 11. The magnetic-resonance system 11 comprises a detector unit formed by a magnet unit 15 with a basic magnet for the generation of a strong and in particular constant basic magnetic field. The magnetic- resonance device 11 also comprises a cylindrical patient receiving region 16 for receiving a patient 12, wherein the patient-receiving region 16 is cylindrically enclosed in a circumferential direction by the magnet unit 15.

In the present case, the patient 12 can be pushed into the patient-receiving region 16 of the magnetic-resonance system 11 via a patient-support apparatus 13 of the magnetic-resonance system 11. To this end, the patient-support apparatus 13 comprises a lie-on table arranged movably within the magnetic-resonance system 11. The patient-receiving region 16 of the magnetic-resonance system 11 has a maximum field of view 17 with an extension in the longitudinal direction of the patient-support apparatus 13 of the magnetic-resonance system 11.

The magnet unit 15 is screened from the exterior via an enclosure housing the magnetic-resonance system 11. The magnet unit 13 furthermore comprises a gradient coil unit for generating magnetic field gradients, which are used for spatial encoding during imaging. The gradient coil unit is controlled via a gradient-control unit. The magnet unit also comprises a radio-frequency antenna unit, which in the case depicted, is embodied as a body coil permanently integrated in the magnetic-resonance system 11, and a radio-frequency-antenna control unit for the excitation of polarization, which is established in a basic magnetic field generated by a basic magnet of the magnet unit 15. The radio-frequency antenna unit is controlled by the radio-frequency-antenna control unit and emits radio-frequency magnetic-resonance sequences in an examination chamber substantially formed by the patient-receiving region 16. The radio-frequency antenna unit is furthermore embodied to receive magnetic-resonance signals, in particular from the patient 12.

The magnetic-resonance system 11 furthermore comprises a measuring unit 18. For example, the measuring unit 18 can be part of the magnet unit 15. The measuring unit 18 can comprise the gradient coil unit and/or the radio-frequency antenna unit.

To control the magnet unit 15, the magnetic-resonance system 11 comprises a control unit 14. The control unit 14 controls the magnetic-resonance system 11 centrally, such as for example the performance of a predefined imaging gradient-echo sequence.

Control information such as for example sequence parameters, and reconstructed magnetic-resonance images can be displayed to a user on a display unit 19, for example on at least one monitor, of the magnetic-resonance system 11. It is also possible for control information to be exchanged between the control unit 19 and a planning unit 20. The planning unit 20 typically comprises the display unit 19. For example, the control unit 14 can provide sequence parameters to the planning unit so that these sequence parameters are displayed to the user on at least one monitor by the planning unit 20. In a further step, the planning unit 20 can, for example after a change in at least one measuring time point of the partial angiographic measurements by the user, define sequence parameters in the background and provide them to the control unit 14. The user can use the planning unit 20 to input information and/or sequence parameters during a measuring process.

The magnetic-resonance system 11 shown can obviously also comprise components conventionally comprised by magnetic-resonance systems 11, for example an injector for the injection of the contrast medium. Moreover, the individual components, in particular the display unit 19, the control unit 14, the measuring unit 18 and the planning unit 20 can have a different relationship to one another and/or be integrated in a higher-ranking unit. In addition, the general mode of operation of a magnetic-resonance system 11 is known to the person skilled in the art and so no detailed description of the further components will be given.

Figure 2:
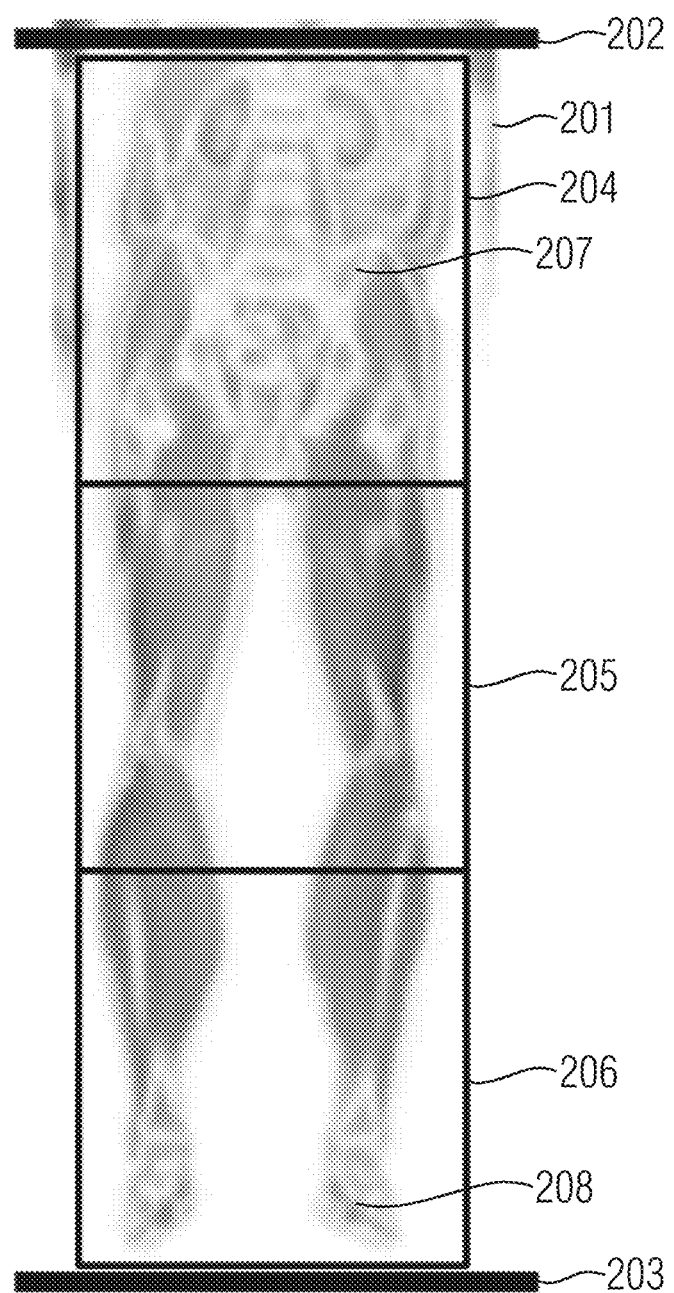
FIG. 2 shows a body region with an upper limit and a lower limit and with partial measuring regions.

The division of the body region 201 into partial measuring ranges is illustrated by way of example in FIG. 2. The body region 201 has an upper limit 202 and a lower limit 203 of the patient 12. By way of example, it intended to perform an angiographic measurement in the body region 201 of the patient 12, wherein the maximum field of view 17 of the magnetic-resonance system 11 is smaller than the body region 201. This in particular means that the extension of the body region 201 in the longitudinal direction of the patient-support apparatus 13 is longer than the extension of the maximum field of view 17 in the longitudinal direction of the patient-support apparatus 13.

Therefore, the body region 201 is divided uniformly into a first partial measuring range 204, a second partial measuring range 205 and a third partial measuring range 206, preferably automatically by the control unit 14. Unlike the case in FIG. 2, the partial measuring ranges 204, 205 and 206 can partially overlap. The first partial measuring range 204, the second partial measuring range 205 and the third partial measuring range 206 in each case include a volume, which, on corresponding positioning of the patient 12 on the patient-support apparatus 13 or, on a corresponding movement of the patient-support apparatus 13 with the patient 12, lies in the maximum field of view 17 of the magnetic-resonance system 11. Also shown are a first station 207 and a second station 208 at which, in each case, a first contrast medium dynamics 307 and a second contrast medium dynamics 308 are acquired.

Figure 3:
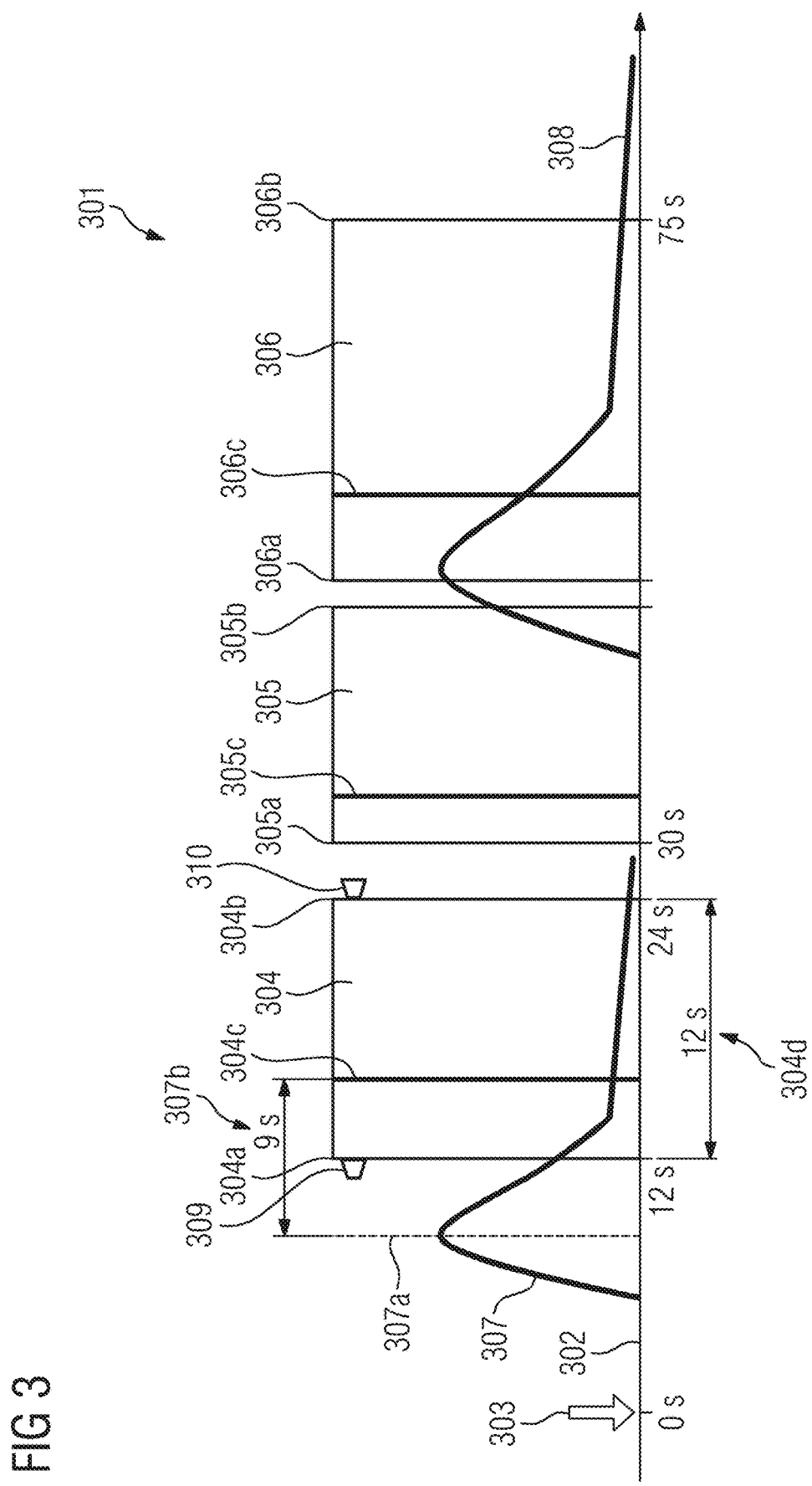
FIG. 3 shows a graphical user interface inter alia with measuring time points and measurement boxes of partial angiographic measurements, contrast medium dynamics and a difference between a maximum-value time point and a mid-time point of a first partial angiographic measurement, a timeline, a time point of a contrast medium injection with a symbol, one symbol each for the time point for holding the breath and the resumption of breathing.

FIG. 3 shows a section on a graphical user interface 301 for the user. The graphical user interface 301 is, for example, part of the display unit 19. A partial angiographic measurement is assigned to each partial measuring range: a first partial angiographic measurement 304 to the first partial measuring range 204, a second partial angiographic measurement 305 to the second partial measuring range 205 a third partial angiographic measurement 306 to the third partial measuring range 206. Each partial angiographic measurement is depicted with a measurement box on a timeline 302, which is, for example, embodied as a horizontal time axis.

The measuring time points of the partial angiographic measurements can, for example, be displayed with numerical values on the graphical user interface 301. For this, it is advisable not to indicate absolute times, but to relate selected measuring time points to a reference time point. A reference time can, for example, be the time point of contrast medium administration 303. Expediently, this time point can be depicted with a symbol indicating the contrast medium administration such as, for example, a picture of a contrast medium injector. The measurement duration of the partial angiographic measurements can optionally also be depicted symbolically by a double arrow. The measurement boxes of the partial angiographic measurements 304-306 are limited by the pairs consisting of the respective measurement start time and measurement end time. Additionally, preferably, measurement start times and measurement end times can be depicted by further markings on the timeline 302, for example by dashed lines.

304a indicates a measurement start time, 304b indicates a measurement end time, 304c indicates a mid-time point and 304d indicates a measurement duration of the first partial angiographic measurement 304.

305a indicates a measurement start time, 305b indicates a measurement end time and 305c indicates a mid-time point of the second partial angiographic measurement 305.

306a indicates a measurement start time, 306b indicates a measurement end time and 306c indicates a mid-time point of the third partial angiographic measurement 306.

307 indicates contrast medium dynamics of the first station 207, 307a indicates the maximum-value time point of the contrast medium dynamics of the first station 307, 307b indicates a difference between the maximum-value time point of the contrast medium dynamics of the first station 307 and the mid-time point the first partial angiographic measurement 304c, and 308 contrast medium dynamics of the second station 208. It is also possible for different symbols to be depicted on the graphical user interface 301 for the user, for example the time point at which a command to hold the breath 309 or resume breathing 310 is played out to the patient during the performance of the angiographic measurement.

Figure 4:
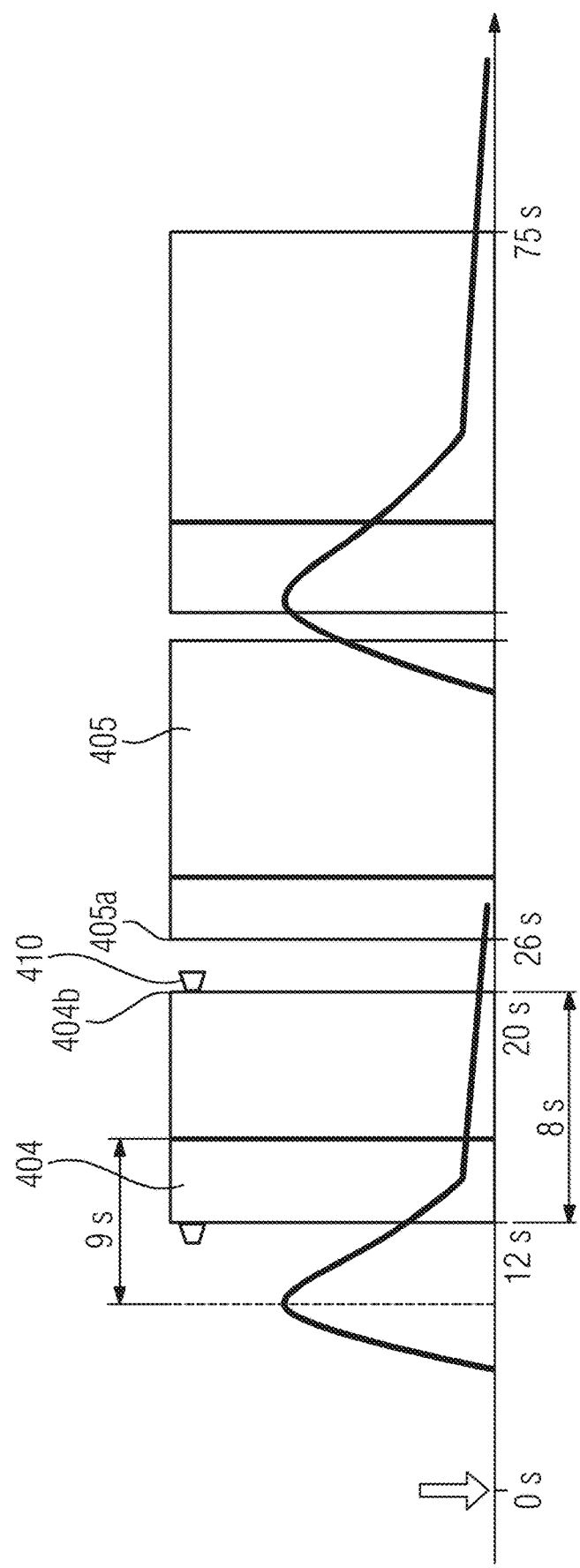
FIG. 4 shows the graphical user interface following a change in the measurement end time of the first partial angiographic measurement compared to FIG. 3.

FIG. 4 shows in a next example embodiment, for example, the changing of the measurement end time 3046b of the first partial angiographic measurement 304, for example by way of interaction with a cursor on the graphical user interface 301 by the user. For reasons of clarity, reference numbers are primarily shown on the features that have changed compared to FIG. 3.

According to an embodiment of the invention, the measurement start time 305a of the second partial angiographic measurement 305 is changed automatically, in particular to the same degree as the measurement end time 304b of the first partial angiographic measurement 304. Preferably, changing the measurement end time 304b of the first partial angiographic measurement 304 only causes the measurement start time 305a of the second partial angiographic measurement 305 to be automatically changed, in particular to the same degree. This causes an automatic definition of the sequence parameters of the first partial angiographic measurement 304 and the second partial angiographic measurement 305 running in the background to take place to a lesser degree than if further measuring time points had been adapted. This is further particularly advantageous for users, who can easily see the impacts of their change, and for performing the angiographic measurement in a short time.

Therefore, FIG. 4 indicates the changed measurement end time 404b of the first partial angiographic measurement 404 following a change, for example by the user using "drag" or "drag and drop", and the subsequently automatically changed measurement start time 405a of the second partial angiographic measurement 405. The other measurement start times remain unchanged when changing the measurement end time 304b of the first partial angiographic measurement 304 only causes the measurement start time 305a of the second partial angiographic measurement 305 to be changed automatically. Furthermore, preferably, the symbol for the time point for the resumption of breathing 410 is shifted. Since the sequence parameters for a change are preferably defined automatically, in FIG. 4 the reference numbers for the first partial angiographic measurement and the second partial angiographic measurement have also changed. In a further embodiment, it is conceivable for the mid-time points 304c and 305c to be adapted as well.

Figure 5:
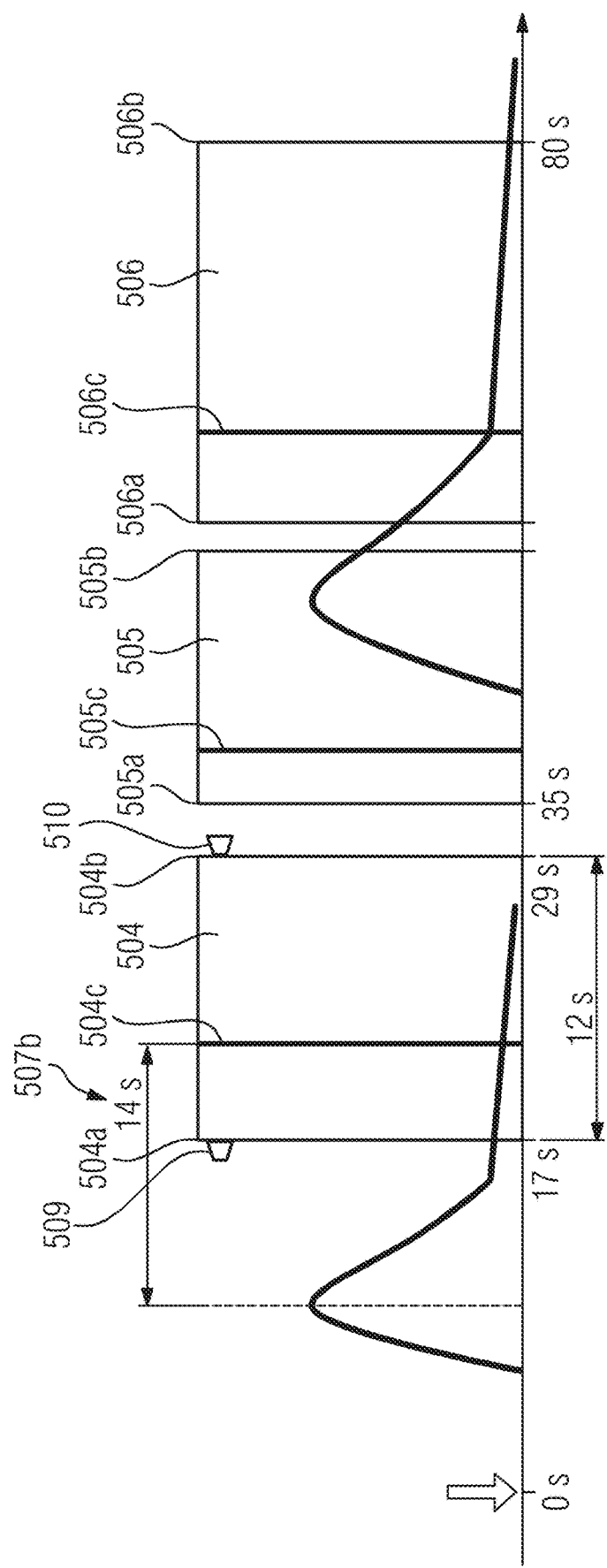
FIG. 5 shows the graphical user interface following a change in the measurement start time of the first partial angiographic measurement compared to FIG. 3.

FIG. 5 shows in a further example embodiment the changing of the measurement start time 304a of the first partial angiographic measurement 304. According to an embodiment of the invention, all other measuring time points are changed as well. This preferably takes place automatically and the change in all the measuring time points is the same in each case, i.e. for example, a shift in all measuring time points by 5 s. Analogous to a change in the measurement start time 304a of the first partial angiographic measurement 304 would, for example, be a simultaneous change in the measurement start time 304a and measurement end time 304b via a selection of the measurement start box of the partial angiographic measurement 304 or a change in a measurement time pause, for example characterized by the measurement end time 305b and the measurement start time 306a. Typically, interaction of this kind is performed by the user with a cursor on the graphical user interface 301.

FIG. 5 depicts, based on the changing of the measurement start time 304a of the first partial angiographic measurement 304 by 5 s, all measuring time points shifted by 5 s: the first partial angiographic measurement 504, the measurement start time 504a, the measurement end time 504b and the mid-time point 504c of the first partial angiographic measurement 504 and the second partial angiographic measurement 505, the measurement start time 505a, the measurement end time 505b and the mid-time point 505c of the second partial angiographic measurement 505 and the third partial angiographic measurement 506, the measurement start time 506a, the measurement end time 506b and the mid-time point 506c of the third partial angiographic measurement 506. The sequence parameters have been updated accordingly in the background. In addition, the symbol for holding the breath 509 and the resumption of breathing 510 has been shifted. In addition, the difference 507b between the maximum-value time point of the contrast medium dynamics of the first station 307 and the mid-time point of the first partial angiographic measurement 504c has changed accordingly.

Figure 6:
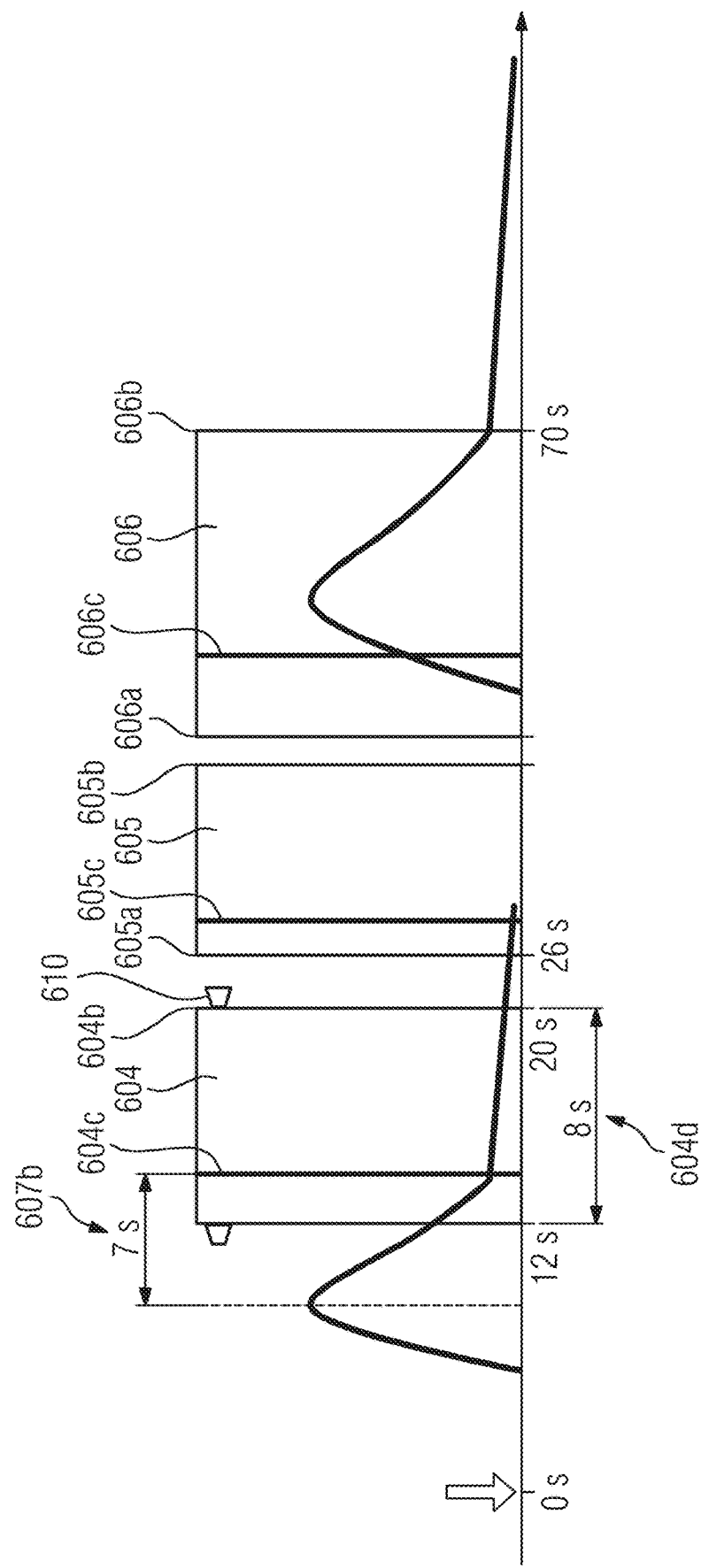
FIG. 6 shows the graphical user interface following a change in the measurement end time of the last partial angiographic measurement compared to FIG. 3.

FIG. 6 shows in a further embodiment according to the invention the changing of the measurement end time 306b of the last partial angiographic measurement 306. This causes the measurement start times of all except for the first partial angiographic measurements and the measurement end times of all the partial angiographic measurements to change automatically and, to be precise, in that the pauses in measurement times, characterized by 304b and 305a and 305b and 306a, are changed not with respect to their duration, but only with respect to the position of the pauses in measurement times. On the other hand, the measurement duration of the partial angiographic measurements, characterized by 304a and 304b, 305a and 305b and 306a and 306b, are changed proportionally in accordance with their proportional share in the overall measurement.

A combination of the examples in FIG. 5 and FIG. 6 is particularly advantageous because, if the user only changes two measurement time points, i.e. first changes the measurement start time of the first partial angiographic measurement and then changes the measurement end time of the last partial angiographic measurement, this causes the measuring time points of all partial angiographic measurements to be defined, preferably taking account of the contrast medium dynamics.

FIG. 6 depicts, based on a change in the measurement end time 306b of the last partial angiographic measurement 306 by −5 s, the constant pauses in measurement times and the partial angiographic measurements with a reduced proportional share of the overall duration: the first partial angiographic measurement 604, the measurement end time 604b, the mid-time point 604c and the measurement duration 604d of the first partial angiographic measurement 604 and the second partial angiographic measurement 605, the measurement start time 605a, the measurement end time 605b and the mid-time point 605c of the second partial angiographic measurement 605 and the third partial angiographic measurement 606, the measurement start time 606a, the measurement end time 606b and the mid-time point 606c of the third partial angiographic measurement 606.

The mid-time points of the partial angiographic measurements have also been changed automatically. The difference between 305a and 304b is the same as the difference between 605a and 604b, likewise the difference between 306a and 305b is the same as the difference between 606a and 605b. In addition, the symbol for the resumption of breathing 610 has been shifted. In addition, the difference 607b between the maximum-value time point of the contrast medium dynamics of the first station 307 and the mid-time point of the first partial angiographic measurement 604c has changed accordingly.

Figure 7:
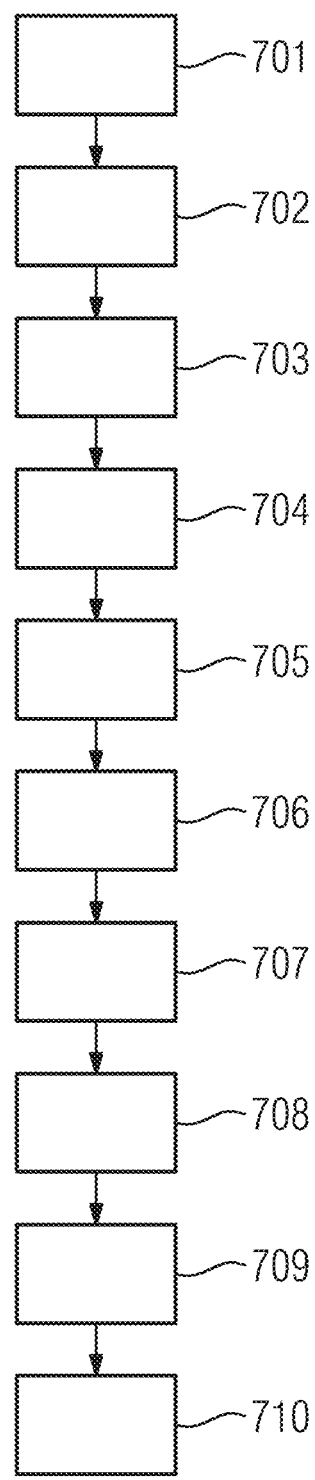
FIG. 7 shows the flowchart of an angiographic measurement without adaptation to an individual patient.

FIG. 7 shows a further example embodiment of the method according to the invention corresponding to a basic set as a starting value for an angiographic measurement. I.e. typically, the basic set has not yet been adapted to a patient's individual circumstances. Contrast medium dynamics that may possibly have been ascertained during a test bolus measurement and/or an anatomical size such as the height of the patient are not further taken into account. The starting point is the division of the body region into four partial measuring ranges. In this case, the angiographic measurement is performed via a test bolus measurement 701, four pre-CM partial angiographic measurements 702-705, the injection of the bolus with contrast medium 706 and four post-CM partial angiographic measurements 707-710. Each one of the four pre-CM partial angiographic measurements 702-705 and post-CM partial angiographic measurements 707-710 is in each case assigned a partial measuring range 'abdomen', 'thigh', 'lower leg' or 'feet' and has a measurement duration. The overall measurement duration of the pre-CM partial angiographic measurements and the post-CM partial angiographic measurements corresponds to 68 s.

Figure 8:
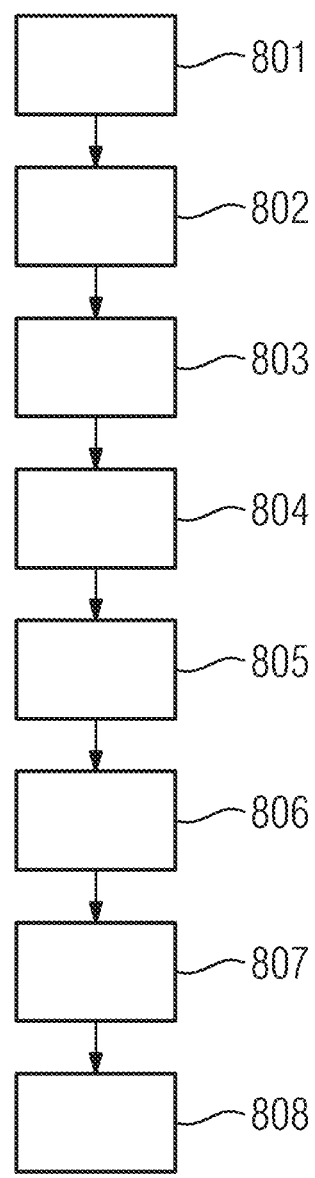
FIG. 8 shows the flowchart of an angiographic measurement with adaptation to a patient with a relatively small height.

In detail, 701-710 characterize the following steps:
701 Test bolus measurement
702 Pre-CM partial angiographic measurement 'abdomen', measurement duration 18 s
703 Pre-CM partial angiographic measurement 'thigh', measurement duration 15 s
704 Pre-CM partial angiographic measurement 'lower leg', measurement duration 15 s
705 Pre-CM partial angiographic measurement 'feet', measurement duration 20 s
706 Contrast medium injection
707 Post-CM partial angiographic measurement 'abdomen', measurement duration 18 s
708 Post-CM partial angiographic measurement 'thigh', measurement duration 15 s
709 Post-CM partial angiographic measurement 'lower leg', measurement duration 15 s
710 Post-CM partial angiographic measurement 'feet', measurement duration 20 s In a further example embodiment, illustrated in FIG. 8, due to the relatively short height, compared to the basic set, the body region 201 of the patient 12 is only divided into three partial measuring ranges, wherein each partial measuring range is in each case assigned one of the pre-CM partial angiographic measurements 802-804 and one of the post-CM partial angiographic measurements 806-808.

Taking into account the circulation time derived from the contrast medium dynamics, wherein said time is substantially comparable to that of a taller patient, the measurement duration of the individual partial angiographic measurements is not changed compared to the basic set. Omitting the fourth partial measuring region and dispensing with the measurement duration of the corresponding fourth partial angiographic measurement at first causes the overall measurement duration of the pre-CM partial angiographic measurements and the post-CM partial angiographic measurements to be significantly reduced to 53 s. In this case, the user extends the measurement duration of all partial angiographic measurements by way of a corresponding extension of the measurement end time of the last partial angiographic measurement 'lower leg' and 'feet' until the overall measurement duration corresponds to 68 s again, for example. The resulting new measurement duration available for each of the three partial angiographic measurements is used by the control unit for measurement in a higher resolution or more signal, in this specific example, the matrix resolution can be increased from 256 to 320 in the partial angiographic measurement 'thigh' and the iPAT factor is reduced from 3 to 2 in the partial angiographic measurement 'lower leg' and 'feet'.

Figure 9:
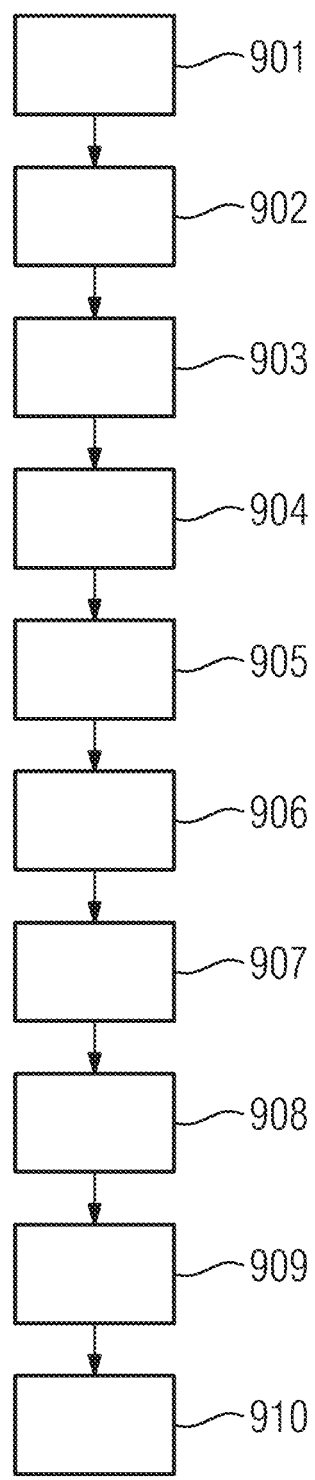
FIG. 9 shows the flowchart of an angiographic measurement with adaptation to a patient with a relatively high circulation time of the contrast medium.

In detail, 801-808 characterize the following steps:
801 Test bolus measurement
802 Pre-CM partial angiographic measurement 'abdomen', measurement duration 23 s
803 Pre-CM partial angiographic measurement 'thigh', measurement duration 19 s
804 Pre-CM partial angiographic measurement 'lower leg' and 'feet', measurement duration 26 s
805 Contrast medium injection
806 Post-CM partial angiographic measurement 'abdomen', measurement duration 23 s
807 Post-CM partial angiographic measurement 'thigh', measurement duration 19 s
808 Post-CM partial angiographic measurement 'lower leg' and 'feet', measurement duration 26 s In this next example embodiment, based on the ascertained contrast medium dynamics of the test bolus-measurement, the patient 12 has a fast circulation time. The corresponding flowchart is shown in FIG. 9. The planned overall measurement duration of the pre-CM partial angiographic measurements and the post-CM partial angiographic measurements of the basic set of 68 s is too long. The user draws the measurement boxes smaller: in this case, the sequence parameters of the partial angiographic measurement are adapted such that the measurement duration is maintained, for example, by increasing of the iPat factor or increasing the slice thickness.

Figure 10:
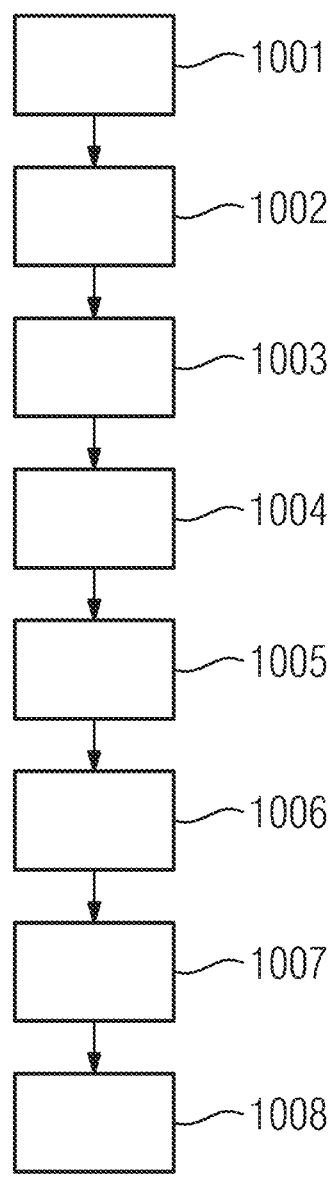
FIG. 10 shows the flow diagram of a method according to an embodiment of the invention.

In detail, 901-910 characterize the following steps:
901 Test bolus measurement
902 Pre-CM partial angiographic measurement 'abdomen', measurement duration 15 s 903 Pre-CM partial angiographic measurement 'thigh', measurement duration 12 s
904 Pre-CM partial angiographic measurement 'lower leg', measurement duration 12 s
905 Pre-CM partial angiographic measurement 'feet', measurement duration 17 s
906 Contrast medium injection
907 Post-CM partial angiographic measurement 'abdomen', measurement duration 15 s
908 Post-CM partial angiographic measurement 'thigh', measurement duration 12 s
909 Post-CM partial angiographic measurement 'lower leg', measurement duration 12 s
910 Post-CM partial angiographic measurement feet, measurement duration 17 s FIG. 10 is a flow diagram of a method according to an embodiment of the invention. The method comprises the method steps 1001-1008, wherein the description of the method steps 1001-1008 also uses parts of the descriptions, including the reference numbers, used in conjunction with the other figures.

Method step 1001 characterizes the acquisition of an anatomical size of the patient 12 and an upper limit 202 and a lower limit 203 of the body region 201.

Method step 1002 characterizes the division of the angiographic measurement into partial angiographic measurements, wherein the control unit 14 divides the body region 201 into a plurality of partial measuring ranges to be measured in succession,
wherein each partial measuring range is assigned to different body regions,
wherein each partial measuring range is no larger than the maximum field of view and each is assigned to a partial angiographic measurement, and
wherein each partial angiographic measurement is assigned measuring time points, including in each case a measurement start time and a measurement end time, so that an overall measurement duration of the angiographic measurement is defined by the measurement start time of the first partial angiographic measurement and the measurement end time of the last partial angiographic measurement.

Method step 1003 characterizes the display of the measurement start times, the measurement duration and the measurement end times of the partial angiographic measurements on a graphical user interface.

Method step 1004 characterizes the changing of the measuring time points, wherein a change in a measuring time point of a partial angiographic measurement causes an automatic adaptation of at least one further measuring time point of another partial angiographic measurement, method step 1005 characterizes the definition of sequence parameters of the partial angiographic measurements based on the changed measurement start times and/or measurement end times such that the partial angiographic measurement can be performed between the associated measurement start time and measurement end time, method step 1006 characterizes the provision of the sequence parameters of the control unit 14 of the magnetic-resonance system 11, method step 1007 characterizes the performance of the partial angiographic measurements, and method step 1008 characterizes the creation of the angiogram using the partial angiographic measurements performed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing an angiographic measurement and creating an angiogram of a body region of a patient in a magnetic-resonance system, the body region being relatively larger than a maximum field of view of the magnetic-resonance system and the magnetic-resonance system including a control unit for controlling performance of the angiographic measurement and creation of the angiogram, the method comprising:
acquiring an anatomical size of the patient and an upper limit and a lower limit of the body region;
dividing the angiographic measurement into partial angiographic measurements, the control unit being configured to divide the body region into a plurality of partial measuring ranges to be measured in succession, each partial measuring range of the plurality of partial measuring ranges being respectively assigned to a different respective partial measuring range of the body region, no larger than a maximum field of view, and assigned to a respective partial angiographic measurement of the partial angiographic measurements, each of the partial angiographic measurements being assigned respective measuring time points, including at least a respective measurement start time and a respective measurement end time, so that an overall measurement duration of the angiographic measurement is defined by the respective measurement start time of a first partial angiographic measurement of the partial angiographic measurements and the respective measurement end time of a last partial angiographic measurement of the partial angiographic measurements;
displaying the respective measurement start time, the respective measurement duration and the respective measurement end time of the respective partial angiographic measurements on a graphical user interface;

changing measurement time points, wherein a change in a respective measuring time point of a respective partial angiographic measurement causes an automatic adaptation of at least one further measuring time point of another partial angiographic measurement;

automatically defining of sequence parameters of the partial angiographic measurements based on the changed measurement time points such that the partial angiographic measurement is performable between an associated measurement start time and measurement end time;

provisioning the sequence parameters of the control unit of the magnetic-resonance system;

performing the partial angiographic measurements; and creating the angiogram using the partial angiographic measurements performed, wherein contrast medium dynamics are acquired on at least one station of the body region via a test bolus measurement with an injected test bolus before the dividing of the angiographic measurement in partial angiographic measurements, and wherein at least one of the contrast medium dynamics and the respective measurement start times, the respective measurement duration and the respective measurement end times of the respective partial angiographic measurements are depicted superimposed on the graphical user interface, and the contrast medium dynamics on the dividing of the angiographic measurement into partial angiographic measurements are used in that a partial angiographic measurement with a first contrast medium velocity derived from the contrast medium dynamics is assigned a shorter measurement duration than a partial angiographic measurement with a second, relatively slower, contrast medium velocity derived from the contrast medium dynamics.

2. The method of claim 1, wherein the changing of the measurement time points includes changing a measuring end time of a non-last respective partial angiographic measurement, causing a measurement start time of a subsequent respective partial angiographic measurement to be changed automatically.

3. The method of claim 1, wherein changing of the measurement time points includes changing a measuring end time of a last respective partial angiographic measurement, causing measurement end times of all partial angiographic measurements and causing measurement start times of all, except for a first respective partial angiographic measurement, to be changed.

4. The method of claim 3, wherein a measurement time pause, including an interval between the measurement end time of a preceding respective partial angiographic measurement and the measurement start time of a subsequent respective partial angiographic measurement, remains constant.

5. The method of claim 1, wherein changing of the measurement start time of a respective non-first partial angiographic measurement causes a respective measurement end time of a preceding respective partial angiographic measurement to be changed automatically.

6. The method of claim 1, wherein changing of the measurement start time of a respective first partial angiographic measurement causes respective measurement start times and respective measurement end times of all respective partial angiographic measurements to be changed automatically.

7. The method of claim 1, wherein simultaneously changing the measurement start time and the measurement end time of a partial angiographic measurement or the measurement end time of a preceding respective partial angiographic measurement and the measurement start time of a subsequent respective partial angiographic measurement causes a change to respective measurement start time and respective measurement end time of all respective partial angiographic measurements.

8. The method of claim 1, wherein the respective measuring time points of the respective partial angiographic measurements each additionally include a mid-time point, corresponding to a time point of acquisition of a center of a k-space, and are displayed on the graphical user interface.

9. The method of claim 8, wherein the mid-time point is changed between respective measurement start time and respective measurement end time of each respective partial angiographic measurement.

10. The method of claim 1, wherein the upper limit and the lower limit of the body region are automatically acquired via recognition of landmarks.

11. The method of claim 1, wherein the body region includes at least body regions 'abdomen', 'thigh' and 'lower leg' and is divided into at least three partial measuring ranges, a first partial measuring range, a second partial measuring range and a third partial measuring range.

12. The method of claim 1, wherein contrast medium dynamics are acquired on two stations of the body region, and wherein at least one station includes feet or a lower leg of the patient.

13. A magnetic-resonance system for performing an angiographic measurement and creating an angiogram of a body region of a patient in a magnetic-resonance system, the body region being relatively larger than a maximum field of view of the magnetic-resonance system and the magnetic-resonance system including a control unit for controlling performance of the angiographic measurement and creation of the angiogram, the magnetic-resonance system comprising:

a planning unit embodied to:
  acquire an anatomical size of the patient and an upper limit and a lower limit of the body region;
  divide the angiographic measurement into partial angiographic measurements and thereby dividing the body region into a plurality of partial measuring ranges to be measured in succession, each partial measuring range of the plurality of partial measuring ranges being respectively assigned to a different respective partial measuring range of the body region and each respective partial measuring range being relatively no larger than a maximum field of view and being assigned to a respective partial angiographic measurement, and each of the partial angiographic measurements being assigned measuring time points, including at least a measurement start time and a measurement end time, so that an overall measurement duration of the angiographic measurement is defined by a respective measurement start time of a first respective partial angiographic measurement of the partial angiographic measurements and a respective measurement end time of a last respective partial angiographic measurement of the partial angiographic measurements, and automatically define sequence parameters of the partial angiographic measurements based on changed measurement time points such that the partial angiographic measurement is performable between an associated measurement start time and measurement end time, provide the sequence parameters of a control unit, display the respective measurement start time, the respective measurement duration and a respective measurement end time of the respective partial angiographic measurements on a graphical user interface, and change the measuring time points, wherein, when a respective measuring time point of a respective partial angiographic measurement is changed, adaptation of at least one further measuring time point of another partial angiographic measurement is performed automatically, the control unit embodied to control the magnetic-resonance system and a measuring unit based on the sequence parameters provided; and the measuring unit to perform the partial angiographic measurements and create the angiogram using the partial angiographic measurements performed, wherein contrast medium dynamics are acquired on at least one station of the body region via a test bolus measurement with an injected test bolus before dividing of the angiographic measurement in partial angiographic measurements, and wherein at least one of the contrast medium dynamics and the respective measurement start times the respective measurement duration and the respective measurement end times of the respective partial angiographic measurements are depicted superimposed on the graphical user interface, and the contrast medium dynamics on the dividing of the angiographic measurement into partial angiographic measurements are used in that a partial angiographic measurement with a first contrast medium velocity derived from the contrast medium dynamics is assigned a shorter measurement duration than a partial angiographic measurement with a second, relatively slower, contrast medium velocity derived from the contrast medium dynamics.

14. A non-transitory computer readable medium including program code for carrying out the method of claim 1 when the program code is run in a computer.

15. A magnetic-resonance system, comprising:

a memory storing program computer-readable instructions; and one or more processors configured to execute the program computer-readable instructions such that the one or more processors are configured to, acquire an anatomical size of a patient and an upper limit and a lower limit of a body region of the patient;

divide an angiographic measurement into partial angiographic measurements, the one or more processors being configured to divide the body region into a plurality of partial measuring ranges to be measured in succession, each partial measuring range of the plurality of partial measuring ranges being assigned to different body regions, no larger than a maximum field of view, and assigned to a respective partial angiographic measurement of the partial angiographic measurements, each of the partial angiographic measurements being assigned respective measuring time points, including at least a respective measurement start time and a respective measurement end time, so that an overall measurement duration of the angiographic measurement is defined by the respective measurement start time of a first partial angiographic measurement of the partial angiographic measurements and the respective measurement end time of a last partial angiographic measurement of the partial angiographic measurements;

display the respective measurement start time, the respective measurement duration and the respective measurement end time of the respective partial angiographic measurements on a graphical user interface;

change measuring time points, wherein a change in a respective measuring time point of a respective partial angiographic measurement causes an automatic adaptation of at least one further measuring time point of another partial angiographic measurement;

automatically define sequence parameters of the partial angiographic measurements based on the changed measurement time points such that the partial angiographic measurement is performable between an associated measurement start time and measurement end time;

provision the sequence parameters of the one or more processors of the magnetic-resonance system;

perform the partial angiographic measurements; and create an angiogram using the partial angiographic measurements performed, wherein contrast medium dynamics are acquired on at least one station of the body region via a test bolus measurement with an injected test bolus before dividing of the angiographic measurement in partial angiographic measurements, and wherein at least one of the contrast medium dynamics and the respective measurement start times, the respective measurement duration and the respective measurement end times of the respective partial angiographic measurements are depicted superimposed on the graphical user interface, and the contrast medium dynamics on the dividing of the angiographic measurement into partial angiographic measurements are used in that a partial angiographic measurement with a first contrast medium velocity derived from the contrast medium dynamics is assigned a shorter measurement duration than a partial angiographic measurement with a second, relatively slower, contrast medium velocity derived from the contrast medium dynamics.

16. The method of claim 4, wherein a measurement duration of all partial angiographic measurements, each respectively relative to a proportional share in an overall measurement duration, is changed.

17. The method of claim 2, wherein changing of the measuring time points includes changing a measuring end time of a last respective partial angiographic measurement, causing measurement end times of all partial angiographic measurements and causing measurement start times of all, except for a first respective partial angiographic measurement, to be changed.

18. The method of claim 17, wherein a measurement time pause, characterized by an interval between the measurement end time of a preceding respective partial angiographic measurement and the respective measurement start time of a subsequent respective partial angiographic measurement, remains constant.

19. The method of claim 6, wherein changing the respective measurement start time of a respective first partial angiographic measurement causes the respective measurement start times and the respective measurement end times of all respective partial angiographic measurements to be changed automatically, without changing overall measurement duration and measurement durations relative to one another.

20. The method of claim 2, wherein simultaneously changing the measurement start time and the measurement end time of a partial angiographic measurement or the measurement end time of a preceding respective partial angiographic measurement and the measurement start time of a subsequent respective partial angiographic measurement causes a change to the respective measurement start time and the respective measurement end time of all respective partial angiographic measurements.

21. The method of claim 2, wherein the respective measuring time points of the respective partial angiographic measurements each additionally include a mid-time point, corresponding to a time point of acquisition of a center of a k-space, and are displayed on the graphical user interface.

22. The method of claim 21, wherein the mid-time point is changed between the respective measurement start time and the respective measurement end time of each respective partial angiographic measurement.

23. The method of claim 2, wherein the upper limit and the lower limit of the body region are automatically acquired via recognition of landmarks.

* * * * *